United States Patent
Moens

(10) Patent No.: US 6,583,317 B1
(45) Date of Patent: Jun. 24, 2003

(54) SYNTHESIS OF ACID ADDITION SALT OF DELTA-AMINOLEVULINIC ACID FROM 5-BROMO LEVULINIC ACID ESTERS

(75) Inventor: Luc Moens, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 287 days.

(21) Appl. No.: 09/691,474

(22) Filed: Oct. 18, 2000

(51) Int. Cl.⁷ ............................................. C07C 229/00
(52) U.S. Cl. .................. 562/567; 560/105; 560/174
(58) Field of Search ..................... 562/567; 560/105, 560/174; 260/349

(56) References Cited

U.S. PATENT DOCUMENTS

| | | | |
|---|---|---|---|
| 3,846,490 A | 11/1974 | Aronova et al. | 260/534 R |
| 4,325,877 A | 4/1982 | Metcalf et al. | 260/349 |
| 5,284,973 A | 2/1994 | Ebata et al. | 562/567 |
| 5,344,974 A | 9/1994 | Descotes et al. | 562/567 |
| 5,380,935 A | 1/1995 | Takeya et al. | 562/567 |
| 5,907,058 A | 5/1999 | Moens | 562/567 |

*Primary Examiner*—James O. Wilson
*Assistant Examiner*—Patrick Lewis
(74) *Attorney, Agent, or Firm*—Paul J. White

(57) ABSTRACT

A process of preparing an acid addition salt of delta-aminolevulinc acid comprising:

a) dissolving a lower alkyl 5-bromolevulinate and hexamethylenetetramine in a solvent selected from the group consisting of water, ethyl acetate, chloroform, acetone, ethanol, tetrahydrofuran and acetonitrile, to form a quaternary ammonium salt of the lower alkyl 5-bromolevulinate; and b) hydrolyzing the quaternary ammonium salt with an inorganic acid to form an acid addition salt of delta-aminolevulinic acid.

8 Claims, No Drawings

SYNTHESIS OF ACID ADDITION SALT OF DELTA-AMINOLEVULINIC ACID FROM 5-BROMO LEVULINIC ACID ESTERS

The United States Government has rights in this invention under Contract No. DE-AC36-83CH10093 between the United States Department of Energy and the National Renewable Energy Laboratory, a Division of the Midwest Research Institute.

BACKGROUND OF THE INVENTION

1. Field of the Invention

The invention pertains to a new process for synthesizing delta-aminolevulinic acid (also known as 5-aminolevulinic Acid) as is hydrochloride salt (DALA.HCl), starting from levulinic acid, which is a product that can be produced from cellulosic materials such as waste paper. In particular, the invention method uses hexamethylenetetramine as a reagent for amination of 5-bromolevulinate ester. The hexamethylenetetramine forms a quaternary ammonium salt with 5-bromolevulinate ester, and the ammonium salt is then decomposed with aqueous hydrochloric acid to form DALA.HCl.

2. Description of the Prior Art

Delta-aminolevulinic acid in the salt form (DALA.HCl) as is known to have potent herbicidal activity against a broad spectrum of weeds and plants, and is also the subject of studies for use as an antitumor compound in humans. The known synthesis of DALA. HCl that are based on levulinic acid as a starting material are difficult to carry out because of the use of undesirable reagents that are either very toxic or that are not atom economical. In addition, in the currently known synthesis of DALA.HCl, a hazardous chemical step is required to "deprotect" the resulting amino group.

U.S. Pat. No. 5,380,935 discloses a process for preparing 5-aminolevulinic acid or a salt thereof, which comprises reacting furfurylamine, of which the amino group has been protected, with an oxygen molecule under irradiation by light in the presence of a sensitizer, hydrogenating the resulting compound in the presence of a metallic catalyst, and hydrolyzing the hydrogenated compound.

A process for preparation of N-acyl-derivatives of 5-amino levulinic acid as well as the hydrochloride of the free acid is disclosed in U.S. Pat. No. 5,344,974. The process condenses 5-hydroxymethyl furfural with a nitrile in acid solution and the N-acyl aminomethyl furfural compound obtained is converted by photooxidation into a N-acyl-5 aminomethyl-5 hydroxydihydro-2,5-furan-2-one and the latter is reduced with zinc in acetic acid under ultrasonic treatment to N-acyl-5 aminolevulinic acid and by acid hydrolysis the 5 aminolevulinic hydrochloride is obtained.

U.S. Pat. No. 5,284,973 disclose a method of making an acid addition salt of delta-aminolevulinic acid by reacting tetrahydrofurfurylamine with phthalic anhydride under an anhydrous condition to introduce a phthalic group which protects the amino group of tetrahydrofurfuryl amine to give N-tetrahydrofurfuryl pthalimide, carbon atoms of the first- and fourth-positions of the obtained N-tetrahydrofurfurylpthalimide are oxidized at 80° C. using sodium periodate as an oxidizing agent and ruthenium chloride hydrate as a catalyst to yield 5-phthalimidolevulinic acid, and the protecting group of the 5-phthalimidolevulic acid is deprotected using an acid to prepare an acid addition salt of delta-aminolevulinic acid.

A method of producing delta-aminolevulinic acid hydrochloride is disclosed in U.S. Pat. No. 3,846,490. The method comprises acylating hippuric acid with monosuccinate acyl-chloride in the medium of 65-picoline, subjecting the thus-obtained c-acyl derivative to hydrolysis and isolating the final product.

U.S. Pat. No. 4,325,877 discloses a method of producing delta-aminolevulinic acid by the use of intermediates of bromoketoesters. However, this patent makes use of metal azides in the amination step to convert the bromoketoesters into delta-aminolevulinic acid.

The foregoing prior art methods do not make use of levulinic acid as a starting material for the synthesis of delta-aminolevulinic acid. The starting materials in these methods are acrylic acid ester, 5-hydroxymethyl-furfural, tetrahdyro-furfurylamine, furfurylamine, and hippuric acid.

A method for synthesizing delta-aminolevulinic acid as its hydrochloride salt is disclosed in U.S. Pat. No. 5,907,058. The method uses sodium diformylamide as a highly reactive and readily accessible reagent for amination of the C-5 position of methyl 5-bromolevulinate. The process generates N,N-diformylamido derivative of the levulinate ester that is hydrolyzed with aqueous hydrochloric acid to generate DALA.HCl as a crystalline solid.

A disadvantage of the sodium diformylamide method of U.S. Pat. No. 5,907,058 is that this reagent generates inorganic residues (i.e. sodium salts) after the final hydrolysis step.

In the art of preparing delta-aminolevulinic acid using the process disclosed in U.S. Pat. No. 5,907,058, the reagent of sodium diformylamide is not yet commercially available and the reagent must be prepared in a separate reactor by treating sodium methoxide with formamide; however, there is the need in preparing DALA.HCl to have a commercially available and inexpensive aminating reagent which is completely hydrolyzed without generating inorganic waste products.

SUMMARY OF THE INVENTION

One objective of the present invention is to provide a process for synthesizing delta-aminolevulinic acid as its hydrochloride salt starting from levulinic acid by utilizing a commercially available and inexpensive reagent which is completely hydrolyzed without generating inorganic waste products.

Another object of the present invention is to provide a process for synthesizing delta-aminolevulinic acid as its hydrochloride salt starting from levulinic acid by utilizing the commercially available hexamethylenetetramine as the amination reagent of 5-bromolevulinic ester to form a quartery ammonium salt which is decomposed with aqueous hydrochloric acid to form DALA:HCl.

A further object of the present invention is to provide a process for synthesizing delta-aminolevulinate acid by using hexamethylenetetramine as the amination reagent of 5-bromolevulinate ester, wherein the hexamethylenetetramine completely hydrolyzes without generating inorganic waste products.

In general, the invention process is accomplished by the use of hexamethylenetetramine as an aminating reagent for amination of the 5-bromolevulinate ester. The reaction of hexamethylenetetramine with 5-bromolevulinate ester forms a quartemary ammonium salt of the 5-bromolevulinate ester. The quarternary ammonium salt is then decomposed with aqueous hydrocholoric acid to form DALA.HCl.

DETAILED DESCRIPTION OF THE INVENTION

A new and less expensive method has been developed for the synthesis of delta-aminolevulinic acid (also called 5-aminolevulinic acid) as its hydrochloride salt (DALA.HCL), starting from levulinic acid, which is a product that can be produced from cellulosic materials such as e.g. waste paper. DALA.HCL is known to have potent herbicidal activity against a broad spectrum of weeds and plants, and is also being studied as an antitumor compound in humans.

In known syntheses of delta-aminolevulinic acid in its hydrochloride salt form using levulinic acid as a starting material, it is difficult to carry out the synthesis due to the use of undesirable reagents for the amination step that are either very toxic, not atom economical, or commercially not available.

For example, in one current process using potassium phthalimide in the amination step for making delta-amino levulinic acid in its hydrochloride salt form, hydrazine is commonly used to "deprotect" the resulting amino group and this results in the disposal of waste that contains phthalic acid, which contains 8 carbon atoms—thereby making the amination step not atom economical, and formidable purification steps are required to isolate DALA. HCl as a crystalline solid.

In another current process for preparing DALA.HCl, sodium diformylamide is used as a reagent for amination of the C-5 position of methyl 5-bromolevulinate. And while the use of sodium diformylamide is significant in that it permits scale-up of the DALA synthesis to commercial scales, this reagent is not yet commercially available and must be prepared in a separate reactor by treating sodium methoxide with formamide.

Further, in addition to the reagent sodium diformylamide not yet being commercially available, this reagent generates inorganic residues (sodium salts) after the final acid hydrolysis step.

The invention synthesis of delta-amino levulinic acid hydrochloride (DALA.HCl) is accomplished by dissolving methyl 5-bromolevulinate in a solvent, and thereafter adding hexamethylenenetetramine to form a quaternary ammonium salt. Thereafter, the mixture is stirred at room temperature to form a suspension. The resulting suspension is concentrated by removing all solvents, whereupon the solid residue is heated in dilute hydrochloric acid to induce hydrolysis, and the reaction mixture is concentrated to provide delta-aminolevulinic acid.

This novel amination step using hexamethylenetetramine as a reagent may be carried out using a series of solvents at room temperature. The solvents are selected from the group consisting of chloroform, acetone, tetrahydrofuran, ethyl acetate, ethanol, acetonitrile or water.

The synthetic pathway of the invention synthesis of delta-aminolevulinic acid (DALA.HCl) is as follows:

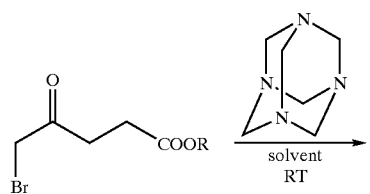

-continued

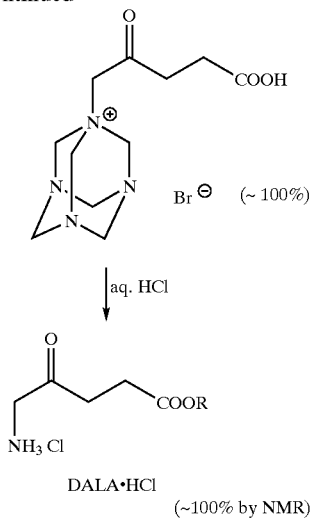

EXAMPLE 1

Hexamethylenetetramine (504 mg) was placed in a 25-mL round bottom flask, and 7 mL of ethyl acetate was added. To this mixture, methyl 5-bromolevulinate (737 mg) was added in one portion via syringe, and the reaction mixture was stirred for 4 h at room temperature to provide the formation of a white suspension. The solvent was removed by rotary evaporation (at room temperature) followed by high vacuum to obtain a dry pale-yellow solid. The latter was dissolved in 30 mL of an aqueous solution of hydrochloric acid (6 M HCl), and the solution was heated at reflux temperature for 4 h. The resulting yellow reaction mixture was then concentrated by rotary evaporation at 55° C., followed by drying under high vacuum at room temperature. This afforded 1.364 g of a yellow-brown solid that was DALA.HCl as analyzed by $^1$H-NMR and by comparing this data with an authentic NMR spectrum of a pure sample of this compound.

EXAMPLE 2

Same as Example 1, except that the amination reaction with hexamethylenetetramine was carried out in the solvent of chloroform, to produce comparable results.

EXAMPLE 3

Same as Example 1, except that the amination reaction with hexamethylenetetramine was carried out in the solvent of acetone, to produce comparable results.

EXAMPLE 4

Same as Example 1, except that the amination reaction with hexamethylenetetramine was carried out in the organic solvent of ethanol, to produce comparable results.

EXAMPLE 5

Same as Example 1, except that the amination reaction with hexamethylenetetramine was carried out in the organic solvent of tetrahydrofuran to produce comparable results.

EXAMPLE 6

Same as Example 1, except that the amination reaction with hexamethylenetetramine was carried out in the organic solvent of acetonitrile to produce comparable results.

EXAMPLE 7

Same as Example 1, except that the amination reaction with hexamethylenetetramine was carried out in water to produce comparable results.

The process of the invention is significant because of the current commercial availability of hexamethylenetetramine and because the novel amination step using hexamethylenetetramine produces a quaternary ammonium salt which does not generate inorganic waste products upon hydrolysis with an inorganic acid.

In the context of the invention, a "lower alkyl" 5-bromolevulinate, will mean a carbon length of 1-5, although one carbon or methyl is preferred.

While ethyl acetate is preferred as the solvent for dissolution of the mixture of hexamethylenetetramine and methyl 5-bromolevulinate, other solvents such as water, chloroform, acetate, ethanol, tetrahydrofuran and acetonitrile may also be used.

The inert atmosphere in which the reaction proceeds is preferably that of Ar gas; however, any of the inert gases will suffice in the context of the invention process.

Additional advantages and modifications to the invention will be apparent to those skilled in the art. Accordingly, the invention in its broader aspects is not limited to the specific details shown and described. Therefore, various modifications and adaptations may be made without departing from the spirit or scope of the inventive concept as defined by the appended claims and their equivalents.

I claim:
1. A process of preparing an acid addition salt of delta-aminolevulinc acid comprising:
    a) dissolving a lower alkyl 5-bromolevulinate and hexamethylenetetramine in a solvent selected from the group consisting of water, ethyl acetate, chloroform, acetone, ethanol, tetrahydrofuran and acetonitrile, to form a quaternary ammonium salt of said lower alkyl 5-bromolevulinate; and
    b) hydrolyzing said quaternary ammonium salt with an inorganic acid to form an acid addition salt of delta-aminolevulinic acid.
2. The process of claim 1, wherein step a) is carried out in an inert gas atmosphere.
3. The process of claim 1 wherein said lower alkyl component of 5-bromolevulinate is selected from at least 1 to 5 carbon atoms.
4. The process of claim 1 wherein said lower alkyl component of 5-bromolevulinate is selected from one carbon atom.
5. The process of claim 1, wherein said solvent is ethyl acetate.
6. The process of claim 2, wherein said inert gas is argon.
7. The process of claim 6, wherein said lower alkyl 5-bromolevulinate is methyl 5-bromolevulinate.
8. The process of claim 7, wherein said inorganic acid is HCl and said acid addition salt of delta-aminolevulinic acid is delta-aminolevulinic acid hydrochloride.

* * * * *